(12) United States Patent
Stevens et al.

(10) Patent No.: US 10,646,448 B2
(45) Date of Patent: May 12, 2020

(54) TABLET

(71) Applicant: Drug Delivery International Ltd., Glasgow, Strathclyde (GB)

(72) Inventors: Howard Norman Ernest Stevens, Strathclyde (GB); Alexander Balfour Mullen, Strathclyde (GB); Fiona Jane MacDougall, Strathclyde (GB); Claire Helen Ordoyno, Strathclyde (GB)

(73) Assignee: Drug Delivery International Ltd., Glasgow, Strathclyde (GB)

( * ) Notice: Subject to any disclaimer, the term of this patent is extended or adjusted under 35 U.S.C. 154(b) by 0 days.

(21) Appl. No.: 15/526,854

(22) PCT Filed: Nov. 16, 2015

(86) PCT No.: PCT/GB2015/053473
§ 371 (c)(1),
(2) Date: May 15, 2017

(87) PCT Pub. No.: WO2016/075497
PCT Pub. Date: May 19, 2016

(65) Prior Publication Data
US 2017/0258731 A1 Sep. 14, 2017

(30) Foreign Application Priority Data

Nov. 14, 2014 (GB) .................................. 1420300.4

(51) Int. Cl.
| | |
|---|---|
| *A61K 9/20* | (2006.01) |
| *A61K 31/343* | (2006.01) |
| *A61K 31/155* | (2006.01) |
| *A61K 31/137* | (2006.01) |

(52) U.S. Cl.
CPC .......... *A61K 9/2095* (2013.01); *A61K 9/2013* (2013.01); *A61K 9/2054* (2013.01); *A61K 9/2068* (2013.01); *A61K 9/2081* (2013.01); *A61K 9/2086* (2013.01); *A61K 31/137* (2013.01); *A61K 31/155* (2013.01); *A61K 31/343* (2013.01)

(58) Field of Classification Search
None
See application file for complete search history.

(56) References Cited

U.S. PATENT DOCUMENTS

| | | | |
|---|---|---|---|
| 4,132,753 | A | 1/1979 | Blichare et al. |
| 5,126,145 | A | 6/1992 | Evenstad et al. |
| 5,310,558 | A | 5/1994 | Pozzi et al. |
| 5,690,959 | A | 11/1997 | Palepu et al. |
| 7,220,430 | B2 | 5/2007 | Ishibashi et al. |
| 7,943,174 | B2 | 5/2011 | Oshlack et al. |
| 2002/0071870 | A1 | 6/2002 | Sharma |
| 2007/0129402 | A1 | 6/2007 | Ueke et al. |
| 2017/0258731 | A1 | 9/2017 | Stevens et al. |

FOREIGN PATENT DOCUMENTS

| | | |
|---|---|---|
| EP | 0074584 A2 | 3/1983 |
| EP | 0097523 A2 | 1/1984 |
| EP | 0277741 A2 | 8/1988 |
| EP | 0418596 A2 | 9/1991 |
| WO | 2000074656 A1 | 12/2000 |
| WO | 2001032148 A1 | 5/2001 |
| WO | 2005041935 A1 | 5/2005 |
| WO | 2005065673 A1 | 7/2005 |
| WO | 2006017159 A1 | 2/2006 |
| WO | 2006035313 A1 | 4/2006 |
| WO | 2007052299 A2 | 5/2007 |
| WO | 2008050987 A1 | 5/2008 |
| WO | 2008157103 A2 | 12/2008 |
| WO | 2011107750 A2 | 9/2011 |
| WO | 2011107755 A2 | 9/2011 |
| WO | 2016075496 A1 | 5/2016 |

OTHER PUBLICATIONS

Kawashima et al.; Pharmaceutical Research, vol. 10, No. 3; pp. 351-355; published 1993.*
International Search Report and Written Opinion for PCT/GB2015/053472 dated Jan. 8, 2016.
International Search Report and Written Opinion for International application No. PCT/GB2015/053472, dated Jan. 8, 2016.
Carter et al. 2002, The Role of Disintegrants in Solid Dosage Manufacturing, 2002-2006 http://www.carterpharmaceuticalconsulting.com/articles/The-role-of-disintegrants.html. 3 pages.
Guo et al., Ion exchange Resins as Drug Delivery Carrier, Journal of Pharmaceutical Sciences, vol. 98 (11)3886-3902. Nov. 2009.
Iloansusi et al., The effect of wax on compaction of microcrystalline cellulose beads made by Extrusion and spheronization. (Drug Development and Industrial Pharmacy)24(1), 37-44. (1998).
Law et al., Use of hydrophilic polymers with microcrystalline cellulose to improve extrusion-spheronization. European Journal of Pharmaceutics and Biopharmaceutics 45, 57-65 (1998).
PEG 8000, Molecular Biology Grade (Polyethylene Glycol 8000), pp. 1-3, <https://www.promega.com/products/biochemicals-and-labware/biochemical-buffers-and-re>. . . Jul. 3, 2019.
Particle Sciences, Hot Melt Extrusion, Technical Brief, vol. 3, pp. 1-2 (2011).
Young et al., Production of spherical pellets by a hot-melt extrusion and spheronization process, International Journal of Pharmaceutics, 242, 87-92 (2002).
Badawy et al., A study on the effect of wet granulation on microcrystalline cellulose particle structure and performance. Mar. 2006, Pharmaceutical Research 23:3, 634-640 (2006).

* cited by examiner

*Primary Examiner* — Jeffrey T. Palenik
(74) *Attorney, Agent, or Firm* — Pepper Hamilton LLP

(57) ABSTRACT

A method of forming an erodible sustained release tablet comprising the steps of:—a. mixing one or more therapeutic agents, one or more disintegrant and one or more molten wax, whilst retaining the wax in molten form; b. solidifying and granulating the mixture; c. forming a tablet by compression of the granules. The invention also relates to a sustained release tablet made according to the method.

21 Claims, 10 Drawing Sheets

TABLET

CROSS-REFERENCE TO RELATED APPLICATIONS

This application is a U.S. national stage filing under 35 U.S.C. § 371 of International Application No. PCT/GB2015/053473 filed Nov. 16, 2015 entitled "TABLET", which claims the benefit of and priority to GB 1420300.4 filed Nov. 14, 2014, the disclosures of which are incorporated herein by reference in their entireties.

The present invention relates to an erodible sustained release tablet and a method of forming such tablets.

Currently, oral delivery is the preferred method for drug administration, however it has a number of problems. Patient compliance can be low due to the need for frequent dosing of drugs with shorter pharmacokinetic half-lives. There is also the issue of varying drug plasma concentration associated with administering several doses per day, which may result in under medication, causing greater risk of breakthrough symptoms, or an overdose with adverse effects, especially in drugs with narrow therapeutic indexes.

Oral sustained release drug delivery systems are designed to release drugs at a predetermined rate to provide a therapeutic effect. Such systems offer a number of advantages over immediate release oral dosage forms, by reducing the frequency of medicine administration, increasing patient compliance and ensuring that optimal plasma levels of drug are maintained, for clinical effect. Clinical applications of oral sustained release formulations include prevention of break through pain in patients receiving opioids and increasing the likelihood of patients taking the full required daily treatment relative to a multiple dosing regimen. Overall, oral sustained release has largely been prompted by major patient compliance issues with conventional oral delivery systems.

It is generally accepted in the art that achieving a sustained release of a drug throughout the gastrointestinal tract in the majority of the population is difficult. An oral drug delivery system must pass through a variety of conditions of, for example, pH and agitation; such conditions being influenced by position in the gastrointestinal tract, and what the subject has eaten or drank. Inter-subject variation also occurs.

Oral sustained release can be achieved using a number of drug delivery systems, including complex matrices and osmotic pumps. Oral sustained release formulations aim to reduce the frequency of administration relative to immediate release formulations and to improve bioavailability of the formulation. Commonly used techniques for achieving sustained release are as follows:— a) Matrix formulations use specific excipients to form a complex matrix which controls the rate of drug release over a defined period of time. The drug is homogeneously distributed throughout the matrix and on contact with the GI fluids, the rate of water ingress and drug solubility ultimately controls the rate at which drug is released from the formulation by diffusion or dissolution/erosion of the matrix.

b) Reservoir devices have a core containing drug, which is coated by a permeable membrane which determines the rate of diffusion of drug from the formulation.

c) Osmotic drug delivery systems use osmotic pressure to control drug release. They allow sustained release unaffected by the physiology of the gastrointestinal tract.

d) Hydrodynamically controlled drug delivery systems such as Madopar™ (a floating capsule containing Levodopa and benserazide) or Valrelease™ (a floating capsule containing Diazepam) is another developing area of sustained release technology. These may consist of granules, powders, capsules, tablets, laminated films or hollow microspheres. These systems have low-density and thus have sufficient buoyancy to float above the contents of the stomach. As the system floats, the drug is slowly released into the gastrointestinal fluid. However these require a sufficient level of fluid to be present to float, which may cause highly soluble drugs to be released too quickly.

There are a great many sustained release formulations on the market, however many of these formulations such as Pfizer's Glucotrol XL and Covera HS are complex to manufacture, while the performance of others can be greatly affected by the changing hydrodynamic conditions, the presence of food and pH, which can vary from individual to individual, and within the individual as a dosage forms transits the gastrointestinal tract.

The inventors have developed an erodible sustained release tablet and method of making same that is simple, yet surprisingly not only provides a consistent release profile of therapeutic agent, but also one that is substantially pH and agitation independent.

In a first aspect of the present invention, there is provided a method of forming an erodible sustained release tablet comprising the steps of:— a. mixing one or more therapeutic agent, one or more disintegrant and one or more molten wax, whilst retaining the wax in molten form;

b. solidifying and granulating the mixture;

c. forming a tablet by compression of the granules.

It has surprisingly been found that this combination of excipients and such a relatively simple formulation process can provide a tablet that demonstrates a controlled release that is independent of pH and/or agitation. Not wishing to be bound by theory, it is considered that the tablet formed according to the present invention provides a controlled sustained release of therapeutic agent by erodible mechanisms. The use of molten wax throughout the mixing process enables a thorough wax coating of particles or agglomerates of the disintegrant and/or therapeutic agent. This wax/disintegrant tablet becomes slowly eroded over time as a result of hydration of the L-HPC which swells and fragments/erodes small fragments from the surface of the tablet matrix. Such a structure eliminates the requirement to include complex pore forming elements, complex matrices and/or complex multilayer formulations that are associated with prior art tablets that provide a controlled release, let alone complex structures associated with the prior art that have been used to provide a pH and/or agitation independent controlled release.

The compressed granules of step c. may entirely form the tablet itself, or the compression may be one of multiple steps in forming a tablet as the compressed granules may form one or more distinct portion of a tablet. For example, the compressed granules may form a core, which alone may form an erodible sustained release tablet, or may be an erodible sustained release core of a tablet with one or more functionalised layer encapsulating the core. Alternatively, the compressed granules may form an erodible sustained release layer that encapsulates a core of a tablet (one or more functionalised layers may be provided between the core and the erodible sustained release layer). Consequently, reference to the tablet made according to the first aspect of the present invention being an erodible sustained release tablet may be understood to mean that the entire tablet made according to that method is an erodible sustained release tablet. Alternatively, the tablet made according to the present invention may have a core and/or one or more layer that is formed from any pharmaceutically accepted method and that provides immediate and/or sustained release of the therapeutic agent provided in that core and/or layer. The core tablet may be optionally capable of immediate or sustained release. Such tablet(s) may be optionally coated for aesthetic or functional purposes and such coatings may further contain API.

Waxes are organic compounds that are insoluble in water and soluble in organic non-polar solvents. Waxes may be of plant or animal origin, or synthetic (such as those derived from petroleum). A wax is a solid at room temperature and has a melting temperature of 30 to 100° C. The wax of the present invention may be any wax capable of being eroded during transit through the gastrointestinal tract and so cannot be liquid at 37° C. The person skilled in the art is capable of determining appropriate waxes, but in the interests of clarity, suitable waxes may have a melting temperature in the range of from 37 to 100° C. For example, the wax may be carnauba wax, paraffin wax, castor wax, beeswax, glycerol behenate, a glycowax or any combination thereof.

The wax is provided in an amount sufficient to largely coat the particles or agglomerates of disintegrant and therapeutic agent. It has been found that increasing the amount of wax in the tablet increases the time over which there is a sustained release of the therapeutic agent. For example, the wax can be provided as 20 to 80% by weight, 30 to 65% by weight, 40 to 50% by weight of the compressed granules.

The disintegrant may be a low-substituted hydroxypropyl cellulose. The IUPAC name for L-HPC is cellulose, 2, hydroxypropyl ether (low substituted). L-HPCs share the same CAS number with hydroxypropyl cellulose (i.e. 9004-64-2). L-HPC however differs from hydroxypropyl cellulose by the fact that it includes less hydroxypropoxy groups in the cellulose backbone. When dried at 105° C. for 1 hour, a L-HPC contains not less than 5.0% and not more than 16.0% by weight of the molecule of hydroxypropoxy groups. The L-HPC may be chosen from the group, but not limited to, LH-11, LH-21, LH-22, LH-32, NBD-021, NBD-020, LH-B1 or any combination thereof.

The disintegrant is provided in an amount that can be coated almost entirely by the wax, but in a sufficient quantity to affect the disintegration of the granules of the tablet. For example, the disintegrant can be provided as 10-80% by weight, 12-50% by weight, 20-35% by weight of the compressed granules of the tablet.

The therapeutic agents of the present invention may be any element or compound that is useful for the treatment of the animal or human body by enteral administration. Indeed, the present invention has wide ranging general applicability to therapeutics, having been demonstrated to be effective for antihyperglycaemic drugs, antifungal drugs and adrenergic receptor agonist decongestants. The methods of the present invention are however particularly useful for formulating therapeutic agents that benefit from a controlled sustained release through the gastrointestinal tract. The person skilled in the art is capable of determining appropriate therapeutic agents, but in the interests of clarity, and not wishing to be restricted further, suitable therapeutic agents may be, metformin hydrochloride, griseofulvin, phenylephrine hydrochloride, opioids, or any combination thereof. Further optional therapeutic agents may be any agent used in methods of therapeutic (including prophylactic) treatment. For example, the therapeutic agent may be any agent for use in the treatment of any one or more of the following:— Central nervous system disorders (e.g. neurogenic pain, stroke, dementia, alzheimer's disease, parkinson's disease, neuronal degeneration, meningitis, spinal cord injury, cerebral vasospasm, amyotrophic lateral sclerosis), cardiovascular disease (e.g. hypertension, atherosclerosis, angina, arterial obstruction, peripheral arterial disease, myocardial pathology, arrhythmia, acute myocardial onfarction, cardiomyopathy, congestive heart failure, coronary artery disease (CAD), carotid artery disease, endocarditis, hypercholesterolemia, hyperlipidemia, peripheral artery disease (PAD), or any combination thereof), Genitourinary disorders (e.g. erectile dysfunction, urinary organ diseases benign prostatic hypertrophy (BPH), renal tubular acidosis, diabetic nephropathy, glomerulonephritis, glomerulosclerosis, urinary tract infection, faecal incontinence, or any combination thereof), ocular disease (e.g. glaucoma, blephartitis, ocular hypertension, retinopathy, conjunctivitis, scleritis, retinitis, keratitis, corneal ulcer, iritis, chorioretinal inflammation, macular edema, xerophthalmia, or any combination thereof), pulmonary disease (e.g. asthma, pulmonary hypertension, acute respiratory distress syndrome, COPD, emphysema, pneumonia, tuberculosis, bronchitis, acute bronchitis, bronchiectasis, bronchiolitis, bronchopulmonary dysplasia, byssinosis, coccidioidomycosis (Cocci), cystic fibrosis, influenza, lung cancer, mesothelioma, or any combination thereof), metabolic diseases (e.g. hypercalciuria, hyperglycemia, hyperinsulinemic hypoglycemia, hyperinsulinism, hyperlysinuria, hypoglycemia or any combination thereof), Exocrine and endocrine diseases (e.g. addison's disease, hypoaldosteronism, cushing's syndrome, diabetes, goitre, hyperthyroidism, hypothyroidism, thyroiditis, pancreatitis or any combination thereof), Hepatic disorders (e.g. hepatitis, non-alcoholic fatty liver disease, cirrhosis, hepatic cancer, primary sclerosing cholangitis, primary biliary cirrhosis, budd-chiari syndrome or any combination thereof), Autoimmune and inflammatory diseases (e.g. multiple sclerosis rheumatoid arthritis, psoriasis, diabetes, sarcoidosis, addison's disease, alopecia areata, amyotrophic lateral sclerosis, ankylosing spondylitis, polyarticular arthritis, atopic allergy, topic dermatitis, autoimmune hepatitis, celiac disease, chagas disease, coeliac disease, cogan syndrome, crohns disease, cushing's syndrome, diabetes mellitus type 1, endometriosis, eosinophilic fasciitis, fibromyalgia/fibromyositis, gastritis, glomerulonephritis, graves' disease. guillain-barre syndrome (GBS), hashimoto's encephalitis, hashimoto's thyroiditis, haemolytic anaemia, idiopathic inflammatory demyelinating diseases, idiopathic pulmonary fibrosis, interstitial cystitis, juvenile idiopathic arthritis, juvenile rheumatoid arthritis, kawasaki's disease, lichen sclerosus, lupus erythematosus, ménière's disease, myasthenia gravis, myositis, narcolepsy, pernicious anaemia, perivenous encephalomyelitis, polymyalgia rheumatica, primary biliary cirrhosis, psoriatic arthritis, reiter's syndrome, rheumatoid fever, sarcoidosis, schizophrenia, sjögren's syndrome, spondyloarthropathy, ulcerative colitis or any combination thereof), Musculoskeletal disorders (e.g. osteoarthritis, osteoporosis, osteonecrosis, arthritis, paget's disease bursitis, costochondritis, tendonitis or any combination thereof), Skin disorders (e.g. acne, alopecia, candidiasis, celluliltis, dermatitis, eczema, epidermolysis bullosa, erythrasma, herpes, erysipelas, folliculitis, impetigo, ringworm, scabies, tinea, trichomycosis or any combination thereof), ENT disorders (e.g.otitis, sinusitis, laryngitis, pharyngitis, laryngitis, meniere's disease, labyrinthitis, or any combination thereof), gastro-intestinal disorders (e.g.irritable bowel syndrome (IBS) necrotizing entercolitis (NEC) non-ulcer dyspepsia, chronic intestinal pseudo-obstruction, functional dyspepsia, colonic pseudo-obstructioduodenogastric reflux, gastroesophageal reflux disease, ileus inflammation, gastroparesis, heartburn, constipation—for example constipation associated with use for medications such as opioids-, colorectal cancer, colonic polyps, diverticulitis, colorectal cancer, barretts esophagus, bleeding in the digestive tract, celiac disease, colon polyps, constipation, crohns disease, cyclic vomiting syndrome, delayed gastric emptying (gastroparesis), diarrhea, diverticulosis, duodenal ulcers, fecal incontinence, gallstones, gas in the digestive tract, gastritis, gastroesophageal reflux disease (GERD), heartburn, hiatal hernia, hemochromatosis, hemorrhoids, hiatal hernia, hirschsprung's disease, indigestion, inguinal hernia, lactose intolerance, peptic ulcers, polyps, porphyria, primary biliary cirrhosis, primary sclerosing cholangitis, proctitis, rapid gastric emptying, short bowel syndrome, stomach ulcers, ulcerative colitis, ulcers, whipples disease, or any combination thereof), acute and/or chronic pain, viral infection, cancer, laryngitis, mastoiditis, myringitis, otitis media, rhinitis, sinusitis, sialadenitis, tonsillopharyngitis, or any combination thereof.

The therapeutic agent is provided in an amount that can be coated essentially entirely by the wax, but a sufficient amount to still be released in a controlled manner.

It is a requirement of the present invention that the wax is in molten form during the mixing process. The skilled person would be well aware when a wax is molten or not, i.e. a molten wax being in liquid form via the application of heat or energy The viscosity of the wax when in liquid form must be sufficiently low for it to be able to coat the particles of disintegrant and therapeutic agent. Any method to enable the wax to remain in molten form during the step of mixing can be used. For example, heat/energy may be applied to the mixture of step a. during the entire mixing step, or intermittently through the mixing step, in order to ensure that the temperature of the mixture is retained above the melting temperature of the wax. The therapeutic agent and the disintegrant may be mixed together to form a pre-mix mixture prior to this pre-mix mixture being added to and mixed with the molten wax. Addition of the pre-mix may be in one step or by a process of trituration.

Alternatively, the therapeutic agent is added to the molten wax and mixed to form a pre-mix mixture, prior to the addition of the disintegrant and a step of further mixing. Addition of the therapeutic agent or disintegrant may be in one step or by a process of trituration.

Alternatively, the disintegrant is added to the molten wax and mixed to form a pre-mix mixture, prior to the addition of the therapeutic agent and a step of further mixing. Alternatively, the disintegrant, the therapeutic agent and the wax are mixed together simultaneously, optionally prior to subjecting the wax/powder mix to heat/energy sufficient to melt the wax.

Any or each of the steps of mixing may be carried out until a suitable dispersal of the components is achieved, eg an even dispersal of therapeutic agent and disintegrant through the wax. Standard content uniformity tests can be undertaken to ensure uniformity of dosage unit, ie an even dispersal of disintegrant and the therapeutic agent. The skilled person is familiar with tests to evaluate uniformity of dosage unit. For example, the US Pharmacopoeia indicates that the uniformity of dosage can be demonstrated by either of two methods, Content Uniformity or Weight Variation, either method can be used in order to determine even dispersal in the present invention. For example, the test for Content Uniformity of preparations presented in dosage units is based on the assay of the individual drug content of the drug substance(s) in a number of dosage units to determine whether the individual content is within the limits set. 10 units are assayed individually using an appropriate analytical method and then the acceptance value is calculated (see Table 2 of Section <905> Uniformity of dosage Units, USP37/NF32 of the US Pharmacopoeia)

In its simplest form, only a therapeutic agent, a disintegrant and a molten wax are mixed in step a. Consequently, the compressed granules formed in step c. may only include a therapeutic agent, a disintegrant and a molten wax.

The mixture will solidify on cooling to below melting point of the system. This may be achieved passively, e.g. by ensuring that no heat/energy source is applied to the mixture so that it returns to ambient temperature. Alternatively, heat/energy may be removed actively from the mixture, for example by applying a circulating cold water jacket around the receptacle in which the mixture is mixed. The step of mixing may continue during the cooling step in order to form granules of mixture.

When granulation occurs with mixing on cooling, it has been found that a better processing is achieved when the granules are then passed through a sieve (typically 1 mm) when warm. Alternatively, granulation of the mixture may be simultaneous with the step of solidifying. For example, the action of stirring the mixture as it cools to a solid will granulate the mixture. Alternatively, the mixture may be extruded and the extrudate sieved or cut into granules prior to being passed through a 1 mm sieve. After sieving granules may be reduced to less than 1 mm.

The tablet is formed by a compression technique, i.e. the granulated mixture is placed into a die for a tablet or for a core of a tablet and pressure applied so as to form the shaped core or tablet. When the granulated mixture is to form an erodible sustained release layer, the core to be encapsulated is inserted into a die and surrounded by the granulated mixture before pressure is applied so as to encapsulate the core within the granulated mixture.

Tablets formed according to the methods of the present invention have been found to provide a controlled and sustained release of therapeutic agent in the normal passage through the gastrointestinal tract. The tablets are able to control the release of therapeutic agent such that it is sustained over, for example, a period of 4 or 12 hours The tablet may be a monolithic formulation. That is, the tablet may be formed essentially as a single unit consisting of only the compressed mixture described above.

Formulations according to the present invention may or may not include a coating on their outer surface or a functional layer provided between the core and the erodible sustained release layer. Potential coatings or functional layers include enteric coatings, coatings including an immediate release portion, cosmetic coatings or a combination thereof and may optionally include a therapeutic agent.

As discussed above, the tablet may be complex in its structure by including the above compressed mixture as part of a more complex structure or as one of its features. For example, the compressed mixture may form the core of a tablet, or a top layer (ie the layer furthest removed from the core) or an intermediate layer. Such more complex structures would enable a tablet to, for example, provide a sustained then pulsed release profile, or an immediate release, sustained release and then pulse release profile. A pulsed release is a rapid release of therapeutic agent after a period of delay of that release.

The tablets formed by the methods of the present invention, are able to provide such advantageous release profiles as discussed above and demonstrated in the examples because of simplicity of manufacture and the ability to form the granules into different layers and cores. This is not possible with the known technologies which use complex osmotic pumps, hydrodynamic or reservoir systems.

Consequently, in a second aspect of the present invention, there is provided a sustained release tablet comprising or consisting of a wax, a disintegrant and a therapeutic agent, wherein the wax coats the particles of the therapeutic agent and of the disintegrant. Mixing and coating is determined to be sufficient when the desired sustained release period is achieved. The combination of these excipients provides an erodible matrix that gradually releases the active ingredient as erosion progresses. The tablet is therefore erodible. The erosion process works independently of pH, agitation and presence of food. As these features are an inherent feature of tablets formed by the first aspect of the present invention, the second aspect of the present invention may be an erodible tablet formed according to the first aspect of the present invention.

All features described for the tablets with respect to the first aspect of the present invention are therefore applicable to the second aspect of the present invention.

Consequently, the tablet may be entirely formed from a wax, a disintegrant and a therapeutic agent, wherein the wax coats the particles of the therapeutic agent and of the disintegrant. Alternatively, the mixture of a wax, disintegrant and therapeutic agent, wherein the wax largely coats the particles or agglomerates of the therapeutic agent and of the disintegrant, may form a core of the tablet with one or more functionalised layer encapsulating the core. Alternatively, the mixture of a wax, disintegrant and therapeutic agent, wherein the wax largely coats the particles or agglomerates of the therapeutic agent and of the disintegrant, may form a layer that encapsulates a core of the tablet (one or more functionalised layers may be provided between the core and the erodible sustained release layer).

The wax may be any wax capable of being eroded during transit through the gastrointestinal tract and so cannot be liquid at 37° C. The person skilled in the art is capable of determining appropriate waxes, but in the interests of clarity, suitable waxes may have a melting temperature in the range of from 37 to 100° C. For example, the wax may be carnauba wax, paraffin wax, castor wax, beeswax, glycerol behenate, a glycowax or any combination thereof.

The wax is provided in an amount sufficient to largely coat the particles or agglomerates of disintegrant and therapeutic agent. For example, the wax can be provided as 20 to 80% by weight, 30 to 60% by weight, or 40-50% by weight of the mixture of a wax, disintegrant and therapeutic agent.

The disintegrants may be any compound capable of accelerating the disintegration of the tablets and/or granules of the tablets after the disintegrant comes into contact with water. The disintegrant may be an organic compound. The disintegrants may be chosen from the group of LH-11, LH-21, LH-22, LH-32, NBD-021, NBD-020, LH-B1 or any combination thereof.

The disintegrant is provided in an amount that can be largely coated by the wax, but in a sufficient quantity to affect the disintegration of the tablet. For example, the disintegrant can be provided as 10-80% by weight, 12-50% by weight, or 20-35% by weight of the mixture of a wax, disintegrant and therapeutic agent.

The therapeutic agents of the present invention may be any element or compound that is useful for the treatment of the animal or human body by enteral administration. Indeed, the present invention has wide ranging general applicability to therapeutics, having been demonstrated to be effective for antihyperglycaemic drugs, antifungal drugs and adrenergic receptor agonist decongestants. The methods of the present invention are however particularly useful for formulating therapeutic agents that benefit from a controlled sustained release through the gastrointestinal tract. The person skilled in the art is capable of determining appropriate therapeutic agents, but in the interests of clarity, and not wishing to be restricted further, suitable therapeutic agents may be, metformin hydrochloride, griseofulvin, phenylephrine hydrochloride, opioids, or any combination thereof.

The therapeutic agent is provided in an amount that can be largely coated by the wax, but in a sufficient quantity to still be released in a controlled manner.

The therapeutic agent and disintegrant may be mixed through the wax.

The tablet may be a monolithic formulation. That is, the tablet may be formed essentially as a single unit consisting of only the compressed mixture described above.

Tablets of the present invention may or may not include a coating on their outer surface or a functional layer provided between the core and the erodible sustained release layer. Potential coatings or functional layers include enteric coatings, coatings including an immediate release portion, cosmetic coatings or a combination thereof and may optionally include a therapeutic agent In a third aspect of the invention, there is provided a sustained release tablet, comprising a wax, a disintegrant and a therapeutic agent wherein that tablet exhibits anti-dose-dumping properties that make it preferable for sustained release of highly potent drugs where dose dumping would be undesirable. This is as a result of the wax integrity being unaffected by alcohol.

Unless indicated to the contrary, all conditions provided herein are measured at a standard temperature and pressure, eg 100 kPa (ie 0.987 atm, 1 bar) and at 20° C.

Unless indicated to the contrary, all amounts of the components of each tablet are provided as % by weight of tablet, when referring to a tablet whole comprising the compressed mixture of therapeutic agent, disintegrant and wax, or by weight of the compressed mixture.

The skilled person is well aware of what is meant by the terms erodible and sustained release and so these terms take their standard meaning in the art. However, erodible may mean a continuous liberation of material (ie both drug and excipient) from the surface of the tablet. Sustained release may mean the constant release of a drug at a pre-determined rate in order to maintain a constant drug concentration over a period of time.

Unless indicated to the contrary, where the invention is defined in terms of features selected from a list, or any combination thereof, each combination is contemplated as being disclosed individually herein as a single optional recited feature that may form part of the present invention. Such single optional recited features may be combined with other features of the present invention, unless context excludes this possibility.

DETAILED DESCRIPTION OF THE INVENTION

The present invention will now be described, by way of example, with reference to the accompanying figures, in which:—

FIG. 1 shows mean drug release (n=6) over time from 500 mg tablets prepared according to the present invention and containing a 10 mg or 100 mg dose of metformin, with the remainder of the tablet being 50:50 (w/w) wax to disintegrant in pH 6.8 buffer.

FIG. 2a shows the release of 100 mg metformin (n=6), from a 500 mg tablet prepared according to the present invention and with a ratio of 50% wax to 50% total powder. The release period is around 4 hours 20 minutes FIG. 2b shows the release of 100 mg metformin from a 500 mg tablet (n=6) prepared according to the present invention and, with the ratio of 55% wax to 45% total powder. The release period is around 7 hours 15 minutes.

Figure 2A:
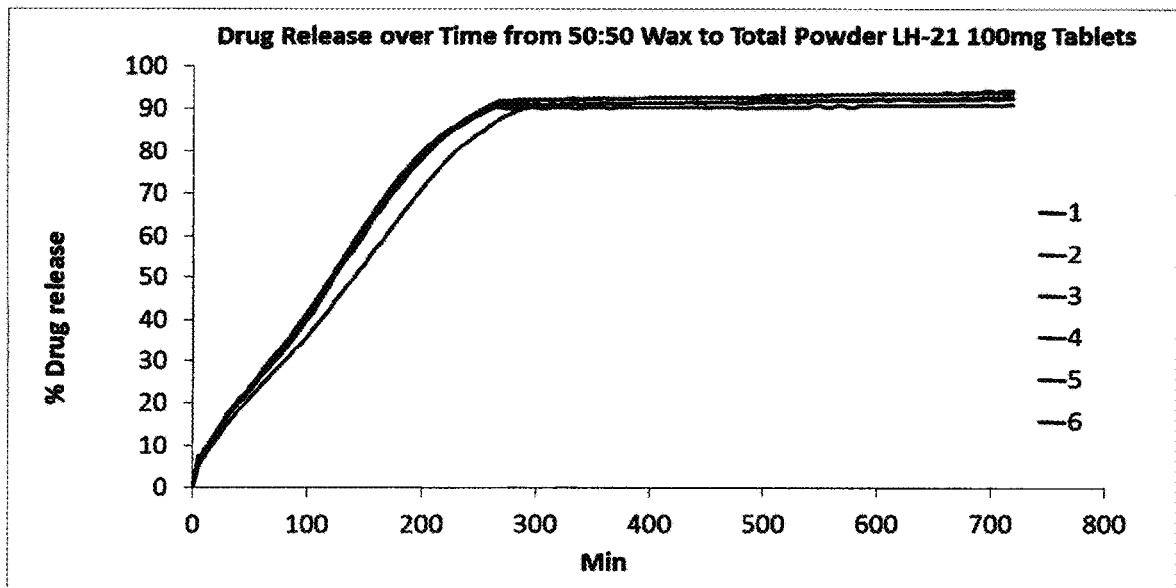
FIG. 2c shows the release of 100 mg metformin from a 500 mg tablet (n=6) prepared according to the present invention and, with the ratio of 56% wax to 44% total powder, release occurs over an average period of around 8 hours.
FIG. 2d shows the release of 100 mg metformin from a 500 mg tablet (n=6) prepared according to the present invention and, with the ratio of 57% wax to 43% total powder, release occurs over an average period of around 9 hours.
Figure 2B:
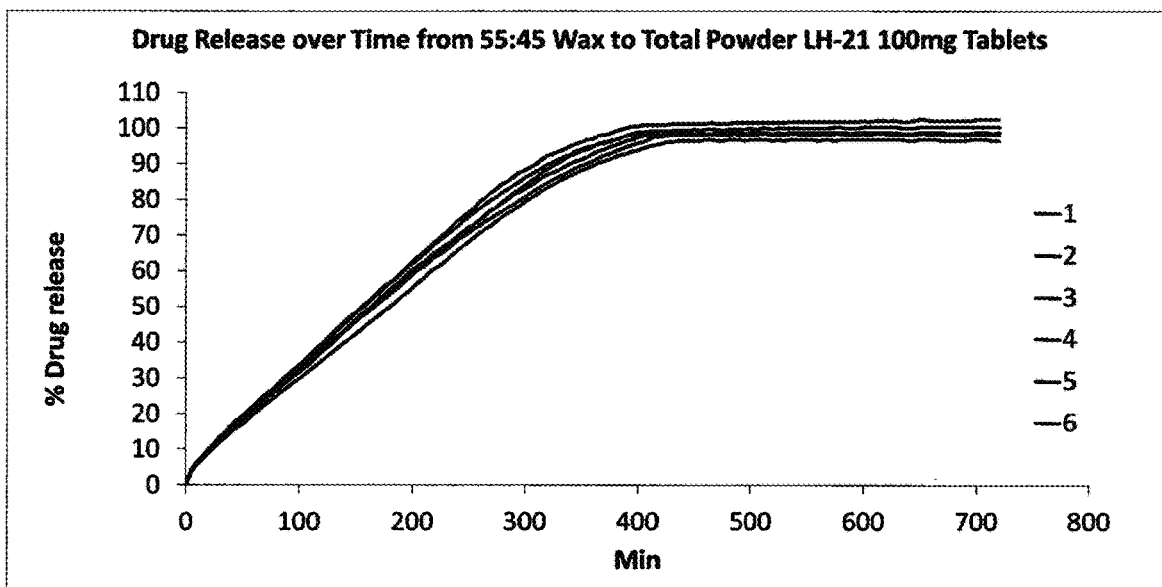
Figure 2C:
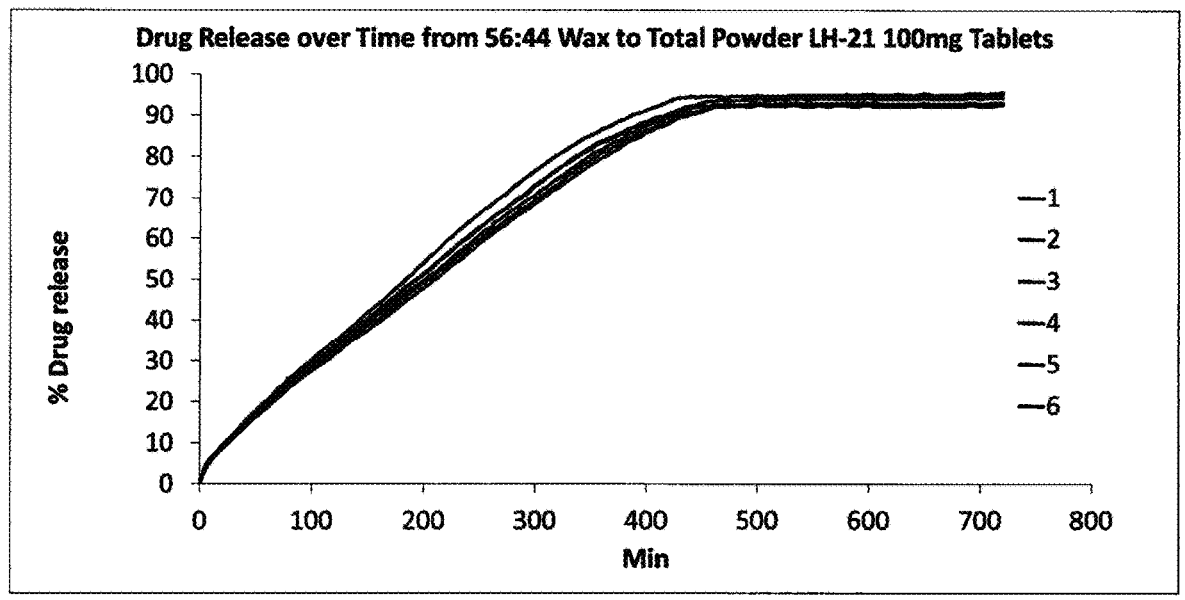
Figure 2D:
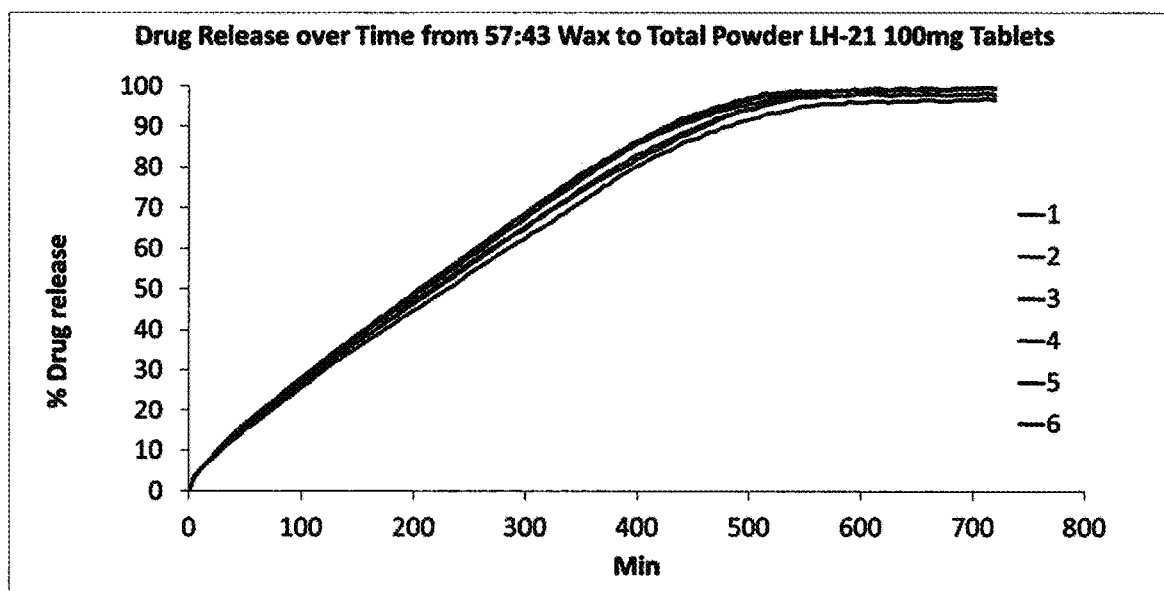
Figure 2E:
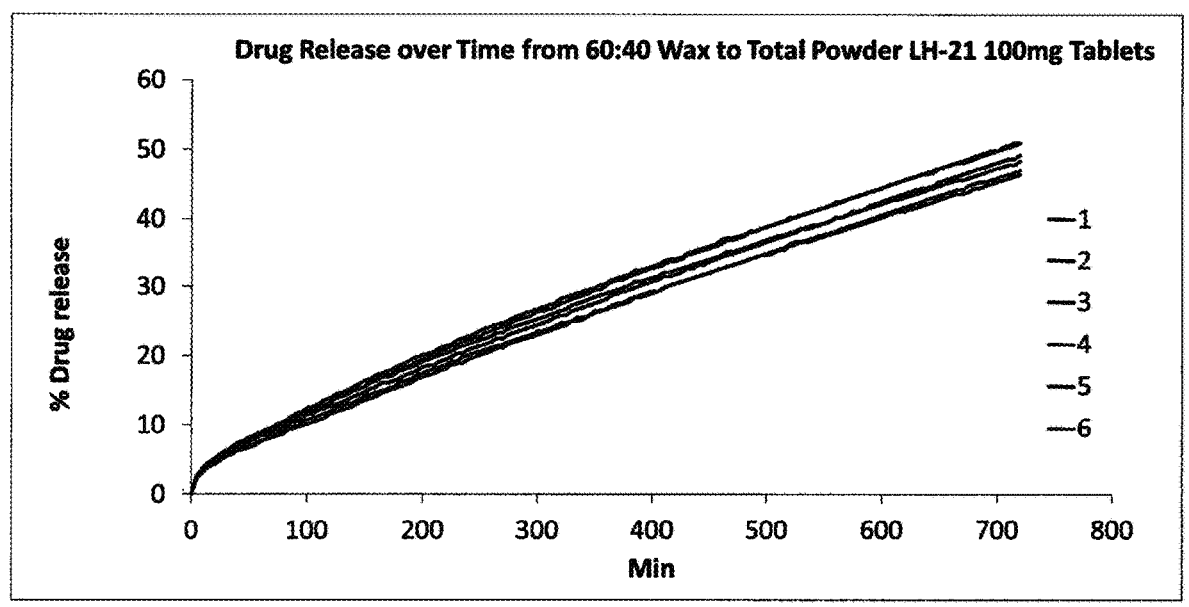

FIG. 2e shows the release of 100 mg metformin from a 500 mg tablet (n=6) prepared according to the present invention and, with the ratio of tablet components altered to 60% wax to 40% total powder. Total drug release was around 48.8%. Full release did not occur within the time frame of the study because of the high wax content of the tablet although it is expected that full release would occur over time.

Figure 3:
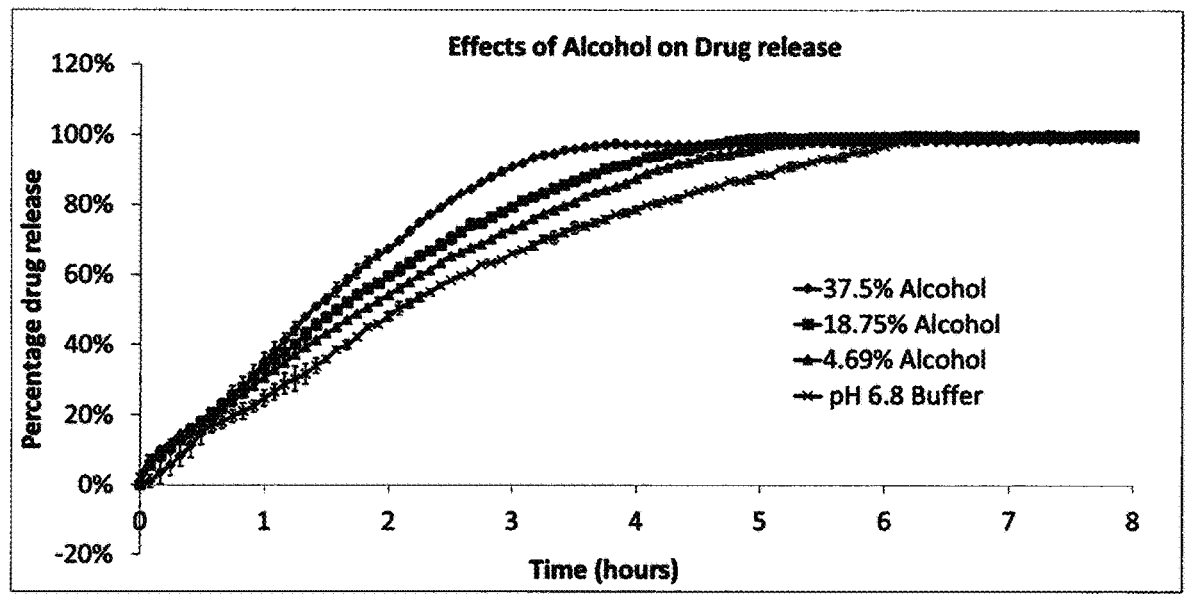

FIG. 3 shows sustained release of phenylephrine in the presence of different concentrations of alcohol in tablets prepared according to the present invention.

Figure 4:
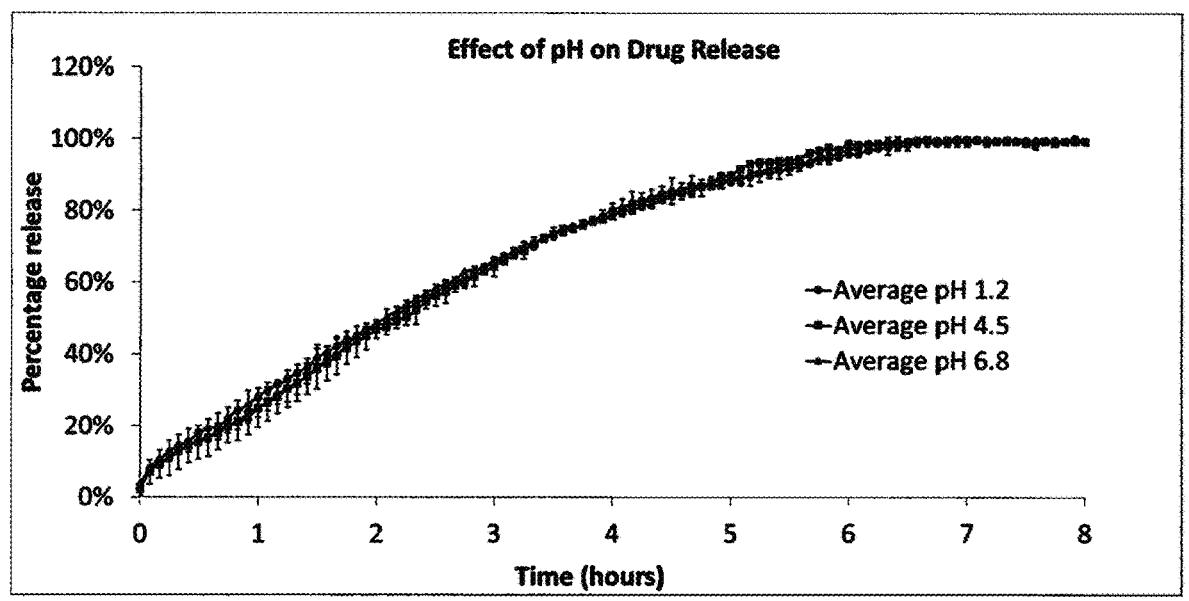

FIG. 4 shows release of API from a sustained release matrix in 3 media at 3 different pHs in tablets prepared according to the present invention. N=2

Figure 5:
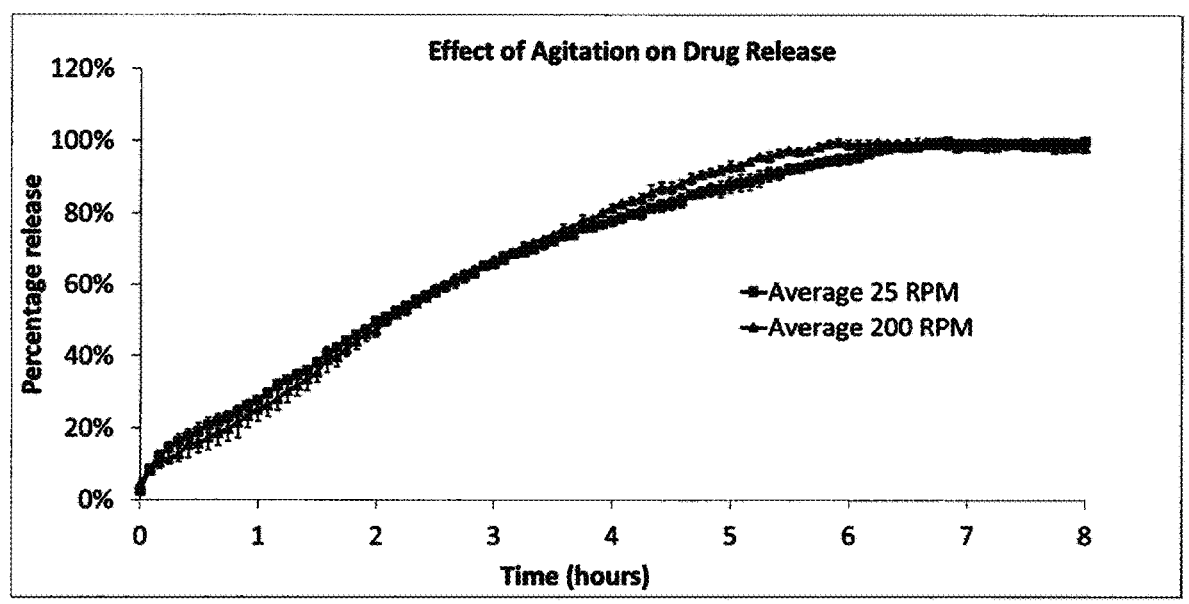

FIG. 5 shows release of API from sustained release matrix from tablets prepared according to the present invention at varying dissolution paddle speeds. N=2

Figure 6:
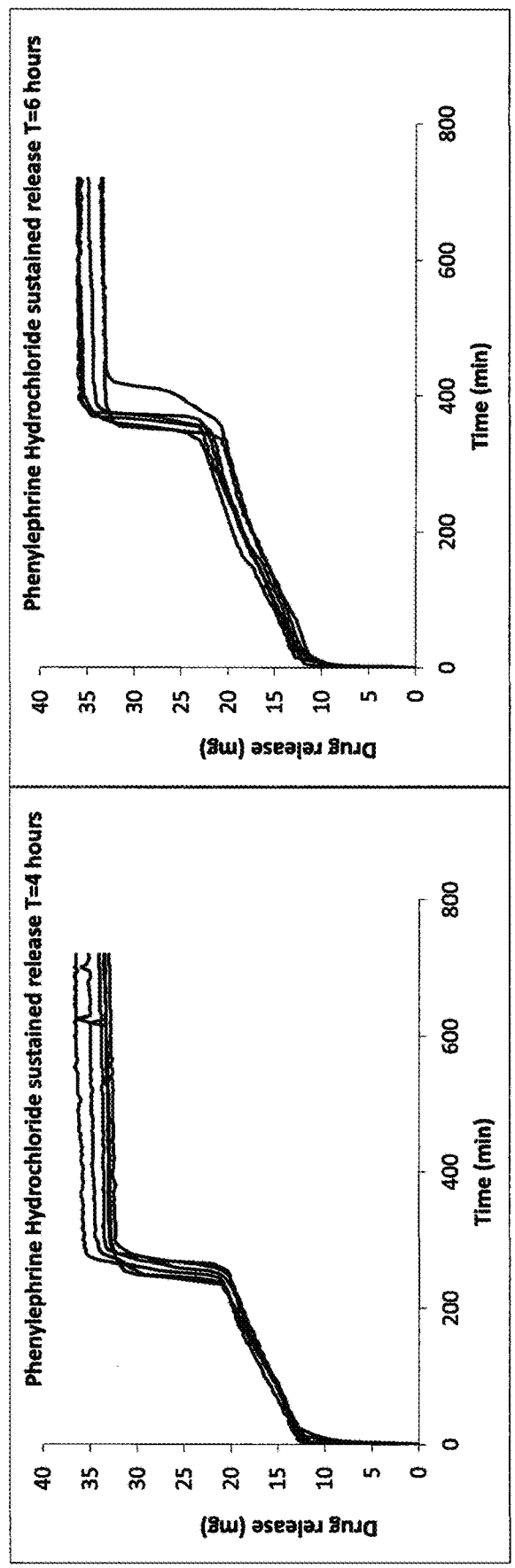

FIG. 6a shows triphasic release combining a 4 hour sustained release layer with an immediate release coating and a phenylephrine core tablet prepared according to the present invention.

FIG. 6b is identical to FIG. 6a but for the fact that the release layer is prepared for a 6 hour sustained release period.

Figure 7:
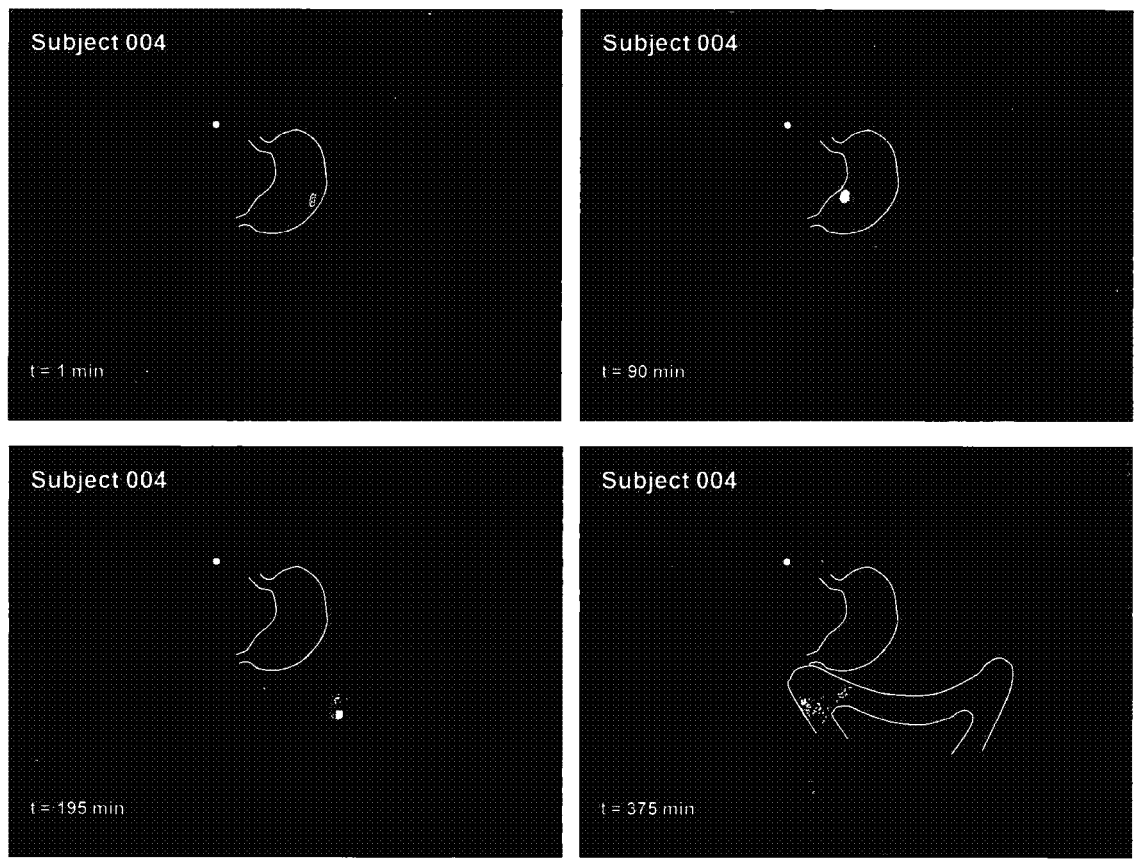

FIG. 7 shows anterior scintigraphic images of key events in the GI transit of a triphasic release tablet prepared according to the present invention with radiolabel contained in the sustained release portion (carried out on Subject 4 of study discussed below under 7.). Images are taken at various times post-dose: (a) 1 min (tablet located in the stomach); (b) 90 min (onset of radiolabel release in the stomach); (c) 195 min (confirmation of tablet gastric emptying) and (d) 375 min (complete radiolabel release in the ascending colon). Stomach and colon outlines are drawn for visualisation purposes only.

Figure 8:
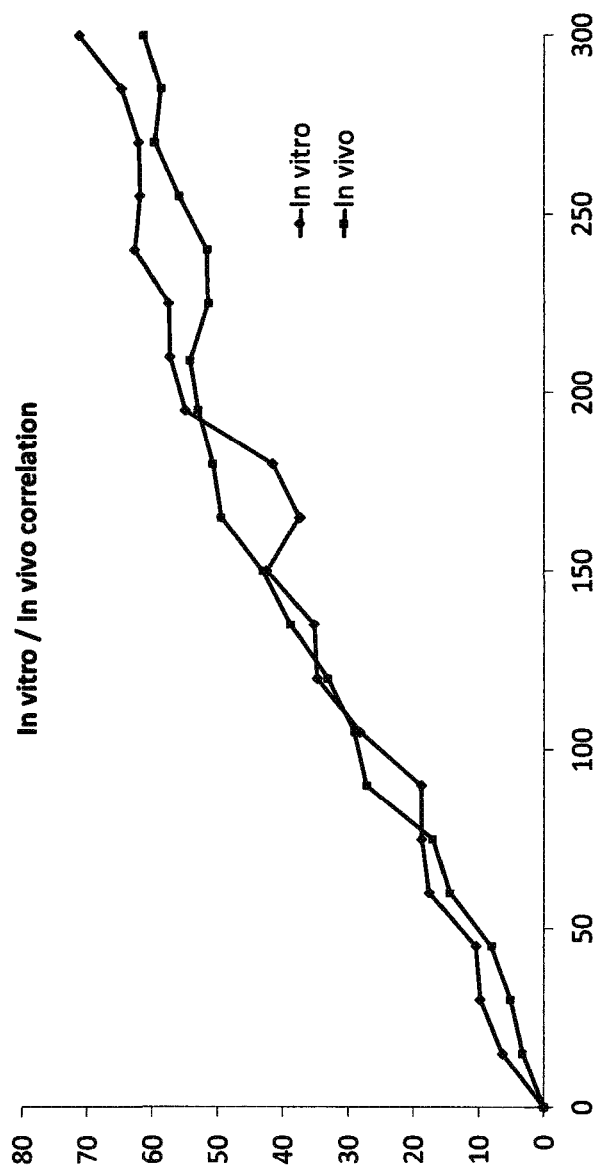

FIG. 8 shows the comparison of average release (%) of radioactivity from the sustained release component of a triphasic release tablet prepared according to the present invention (n=3) in vitro and in healthy volunteers (n=6) showing good in vitro/in vivo correlation.

1. PREPARATION OF TABLETS

Tablets prepared according to the present invention and tested in studies discussed below include various combinations of the following materials:— Metformin hydrochloride (batch 122110) was obtained from Spruyt Hillen BV (IJsselstein, The Netherlands). Griseofulvin (batch 10130-B03) was purchased from Fagron (Terressa, Spain). Phenylephrine hydrochloride (batch 031M1736V) was purchased from Sigma-Aldrich (St. Louis, U.S.A.). Glyceryl behenate, also referred to as GB (batch 134916) was purchased from Gattefosse (St-Priest, France). The L-HPC disintegrants were obtained from Shin Etsu (Tokyo, Japan).

Granules used to form a wax matrix were produced by melt granulation using glyceryl behenate and disintegrant in different ratios dependent on the target release period.

Glyceryl behenate (ie the wax) was melted by heating to 90° C. Once melted, the API (ie metformin hydrochloride, griseofulvin or phenylephrine hydrochloride) was added to the molten wax and mixed to form a dispersion. The disintegrant (ie L-HPC) and more of the API was then gradually added to the dispersion, and resultant mixture combined thoroughly using a spatula. To aid mixing, heat was maintained under the beaker until a consistent blend was achieved. Once fully combined the mixture was removed from the heat and granulated by stirring to break up the mixture as it cooled. The resultant granules were then milled while warm through a 1 mm sieve to produce granules of more regular dimension. Granules were compressed into a tablet using a 10 mm biconvex die.

The final tablets used in the studies below were prepared with varying ratios of API: Low-substituted hydroxypropyl cellulose (L-HPC): glycerol behenate prepared according to the above description in order to deliver sustained release drug delivery over a range of time periods. The ratios in the tablets for each study are provided below. Unless indicated otherwise, all weights are provided in mg.

2. IN VITRO DRUG RELEASE STUDIES

Dissolution studies were carried out on tablets prepared according to the present invention using an automated ADTB USP dissolution type II apparatus (TDT08L Bath 1105230, Electrolab Inc., Cupertino, USA), with paddle operated at 50 rpm, at 37° C.±0.5° C. Dissolution was carried out in 900 ml of pH6.8 phosphate buffer. Samples of dissolution media were withdrawn every 5 minutes and measured by UV analysis using an SP700 High Performance UV Visibility Spectrometer (T70+18-1815-1-0054, PG Instruments Ltd., Wibtoft, U.K.). Appropriate standard samples for 100 mg and 10 mg metformin per tablet preparations were measured prior to dissolution, using pH 6.8 phosphate buffer as a blank, to provide absorbance for 100% drug release.

3. EFFECT ON RELEASE PROFILE WITH VARIED AMOUNT OF API

An in vitro drug release study was carried out according to 2. above on two sets of 500 mg tablets, both prepared according to the present invention and in accordance with proportions of ingredients presented in Table 1. Both sets of tablets included equal amounts by weight of glyceryl behenate to L-HPC, whilst one set of tablets included almost 10 times the amount by weight of metformin HCL. Results shown are mean results from 6 repeated studies.

TABLE 1

| | Ratio of Components | | |
|---|---|---|---|
| API | GB | disintegrant | API |
| 10 mg Metformin•HCl* | 48.7 | 48.7 | 2.6 |
| 100 mg Metformin•HCl* | 37.2 | 37.2 | 25.6 |

*dose based on metformin and not metformin•HCl

Figure 1:
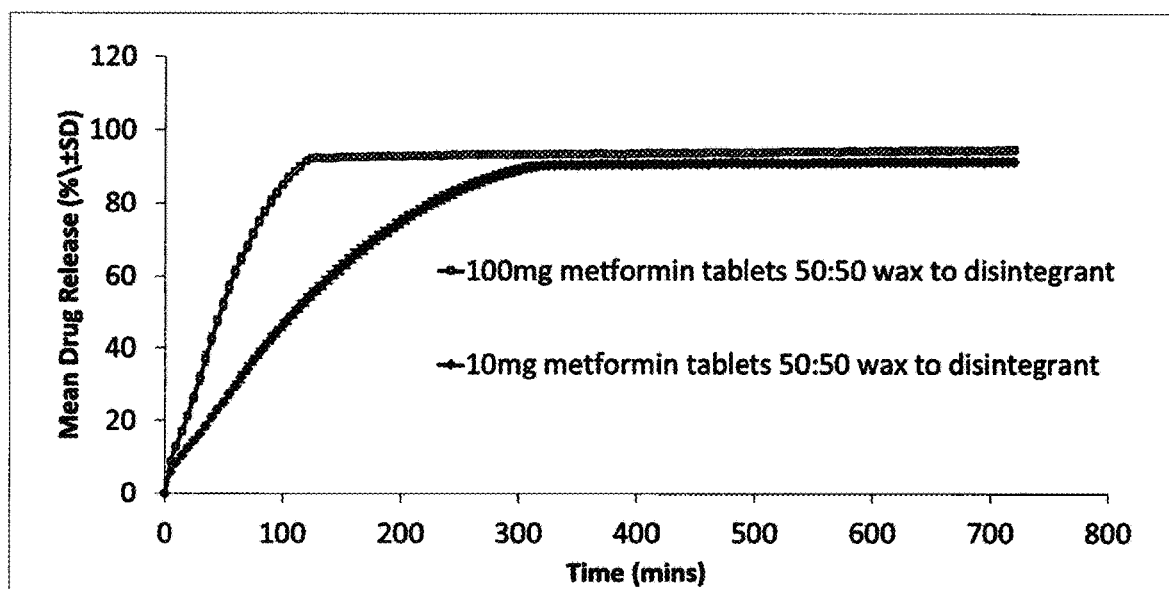

Whilst an increase in dose of API in the tablet results an elevated rate of release of API from the tablet, it can be seen that the amount of API does not affected the ability to provide sustained release, ultimately close to total release of the API. The results of this study are provided in FIG. 1.

4. EFFECT ON RELEASE PROFILE WITH VARIED RATIO OF WAX TO DISINTEGRANT/API

An in vitro drug release study was carried out according to 2. above on 5 sets of tablets, all tablets being prepared according to the present invention and in accordance with proportions of ingredients presented in Table 2a to 2e. Results are provided in FIGS. 2a to 2e, corresponding to the tablets of Tables 2a to 2e, respectively.

TABLE 2a

| | Ratio of Components | | |
|---|---|---|---|
| API | GB | disintegrant | API |
| Metformin•HCl* | 50 | 24.4 | 25.6 |

TABLE 2b

| | Ratio of Components | | |
|---|---|---|---|
| API | GB | disintegrant | API |
| Metformin•HCl* | 55 | 19.4 | 25.6 |

TABLE 2c

| | Ratio of Components | | |
|---|---|---|---|
| API | GB | disintegrant | API |
| Metformin•HCl* | 56 | 18.4 | 25.6 |

TABLE 2d

| | Ratio of Components | | |
|---|---|---|---|
| API | GB | disintegrant | API |
| Metformin•HCl* | 57 | 17.4 | 25.6 |

TABLE 2e

| | Ratio of Components | | |
|---|---|---|---|
| API | GB | disintegrant | API |
| Metformin•HCl* | 60 | 14.4 | 25.6 |

* dose based on metformin and not metformin.HCl

Increasing the wax to powder (ie the combination of API and LHPC) ratio had the effect of extending the period of drug release. The higher the percentage of wax, the longer the period of sustained release (see FIGS. 2a-e). Additionally, it can be seen that the formulations of the present invention provide a good consistent release profile from the fact that that the repeated tests for each table provide almost identical time/release curves in each of the tables 2a-2e.

5. EFFECT ON RELEASE PROFILE WHEN IN PRESENCE OF ALCOHOL

An in vitro drug release study was carried out according to 2. above, on tablets being prepared according to the present invention and in accordance with proportions of ingredients presented in Table 3. The study was repeated, but on each repetition with the addition of increasing amounts of alcohol being added to the phosphate buffer in which dissolution occurs. Results are provided in FIG. 3.

TABLE 3

| | Ratio of Components | | |
|---|---|---|---|
| API | GB | Disintegrant | API |
| Phenylephrine | 50 | 46.7 | 3.3 |

One of the potential problems with sustained release formulations is ethanol induced dose dumping, where the controlled release mechanism fails in an ethanol solution causing all or most of the drug to be released over a very short period of time. This can be very hazardous when used for delivery of potent or toxic drugs. The sustained release mechanism of this invention is substantially unaffected by the presence of alcohol even at high concentrations. (see FIG. 3)

6. EFFECT ON RELEASE PROFILE WHEN IN VARIED pH ENVIRONMENT

An in vitro drug release study was carried out according to 2. above, on tablets being prepared according to the present invention and in accordance with proportions of ingredients presented in Table 4. The study was repeated, but on each repetition with the phosphate buffer being controlled so as to present a decreasing pH environment in which dissolution occurs. Results are provided in FIG. 4.

TABLE 4

| | Ratio of Components | | |
|---|---|---|---|
| API | GB | Disintegrant | API |
| Phenylephrine | 50 | 46.7 | 3.3 |

7. EFFECT ON RELEASE PROFILE BY AGITATION

An in vitro drug release study was carried out according to 2. above, but with the dissolution paddle operating at varying speeds in order to replicate different conditions of agitation that may be experienced by a tablet as it passes through the GI tract. The studies were carried out on tablets being prepared according to the present invention and in accordance with the proportions of ingredients presented in Table 5.

TABLE 5

| | Ratio of Components | | |
|---|---|---|---|
| API | GB | Disintegrant | API |
| Phenylephrine | 50 | 46.7 | 3.3 |

Gut motility and degrees of compaction of matter in the gut can vary greatly between individuals and between different states of health of an individual. These changes can vary the amount of agitation that a tablet experiences as it transits through the GI tract. The above studies demonstrates that the present invention works independently of agitation. See FIG. 5.

8. IMMEDIATE, SUSTAINED AND PULSED RELEASE

An in vitro drug release study was carried out according to 2. above, all tablets being prepared with one layer according to formulation described in 1. above and that layer being in accordance with proportions of ingredients presented in Table 6. Each tablet was constructed with a core comprising 10 mg Phenylephrine HCl; 4.5 mg Crosscarmellose sodium; 2.25 mg Kollidon 3; 27.35 mg lactose monohydrate and 0.9 mg Magnesium stearate. The phenylephrine hydrochloride, croscarmellose sodium, Kollidon 30 and lactose monohydrate were mixed by hand in a suitable container for approximately three minutes. Magnesium stearate was then added and the blend mixed for a further three minutes before passing through a 180 µm sieve. 44 mg of the tablet blend was weighed and mixed with 3 mg of lactose. The tablets were compressed using a tablet press and a 5.9 mm bi-convex punch and die set. The tablets' weights were then measured to confirm that they met the weight specification of between 42.5-47.5 mg. The core being encapsulated in a layer prepared for either 4 or 6 hour sustained release, this encapsulated core itself being coated in a further layer comprising 10 mg of Phenylephrine HCl in a standard Opadry solution. Approximately 1.5 g of Opadry clear was weighed and gradually added to 30 mL of sterile water while mixing on a magnetic stirrer/hotplate.

Approximately 400 mg of phenylephrine hydrochloride was weighed and added to a 2 mL amber volumetric flask, followed by 1 mL ethanol. A magnetic stirrer was added and the contents of the flask mixed until fully dissolved. The magnetic stirrer was then removed and the flask made to volume with the Opadry clear solution. The solution was then transferred to an amber HPLC vial with a micro magnetic stirrer added and mixed until required for tablet manufacture. 50 µL of the coating was applied to the surface of the tablet.

The core and outer layer being prepared to facilitate immediate release of API when in contact with aqueous solutions of the GI tract. For the formulations prepared for a 6 hour sustained period, the layer providing sustained release is a larger (400 mg) barrier layer than in the 4 hour sustained period (300 mg).

Results are provided in FIG. 6a for the tablet prepared for a 4 hour release profile and in FIG. 6b for the tablet prepared for a 6 hour release profile.

TABLE 6

|  |  | Ratio of Components |  |  |
| --- | --- | --- | --- | --- |
|  | API | GB | disintegrant | API |
| T = 4 hours | Phenylephrine•HCl | 45 | 50 | 5 |
| T = 6 hours | Phenylephrine•HCl | 45 | 51.2 | 3.8 |

The formulations studied here demonstrate further possibilities for expanding the use of the sustained release technologies of the present invention so as to provide a long acting formulation, or to allow delivery of a combination of drugs if appropriate. One such example, as studied here, is a tri-phasic release tablet that provides an immediate dose-release followed by sustained release and a final burst-release from a tablet core providing a potential for a 'once a day' formulation.

9. CLINICAL EVALUATION

A two-arm clinical study was designed to investigate the in vivo behaviour of a triphasic release formulation which delivers an immediate 10 mg dose of phenylephrine followed by a 15 mg sustained release dose delivered over a 5 hour period and a 10 mg delayed release pulse from a core tablet. Formulated as discussed above in the paragraph numbered 8.

Qualitative and quantitative scintigraphic methods were used to assess the gastrointestinal transit of the tablets and their disintegration properties.

In study arm 1 the core tablet was radiolabelled to allow visualisation of release from the tablet core, in the second arm, radiolabel was incorporated into the sustained release layer to demonstrate the consistency of erosion.

The results for analysis of study arm 1 are provided in Table 7. The mean times for onset of release and complete radiolabel release from the core tablet was 433.5±13.4 min and 562.5±73.5 min respectively post dose (n=5). Identical tablets were also studied in vitro under the procedure outlined in 2. above, providing a slightly longer period of core release observed in vitro and one that occurred at 300 minutes.

The data in the table below shows the time and location of onset of release from the core tablet showing highly reproducible burst time demonstrating the consistency of erosion of the sustained release layer despite location within the GI tract.

TABLE 7

| Subject No | Onset of release (min) | Site of onset | Completion of release (min) | Site of completion | Time from onset to complete release (min) |
| --- | --- | --- | --- | --- | --- |
| 001 |  |  |  |  |  |
| 002 | 427.5 | ICJ | 607.5 | ICJ | 180.0 |
| 003 | 427.5 | AC/TC | 592.5 | AC/TC | 165.0 |
| 004 | 427.5 | ICJ | 517.5 | AC | 90.0 |
| 005 | 427.5 | AC | 457.5 | AC | 30.0 |
| 006 | 457.5 | DC | 637.5 | DC | 180.0 |
| Mean | 433.5 |  | 562.5 |  | 129.0 |
| Median | 427.5 |  | 592.5 |  | 165.0 |
| Min | 427.5 |  | 457.5 |  | 30.0 |
| Max | 457.5 |  | 637.5 |  | 180.0 |
| St Dev | 13.4 |  | 73.5 |  | 66.7 |
| N | 5 | 2 ICJ; 1 AC; 1 AC-TC; 1 DC | 5 | 1 ICJ; 2 AC; 1 AC/TC; 1 DC | 5 |

ICJ—ileocaecal junction; AC—ascending colon AC/TC—ascending/transverse colon;

TC—transverse colon; DC—descending colon

The above table shows time and location of radiolabel release from core tablets in the triphasic release tablet in healthy volunteers (n=5)

The mean time for onset of radiolabel release from the sustained release layer (ie arm 2) was 75.0±22.7 min. Results are provided in Table 8. Complete release was from the sustained release layer was observed in the colon for all subjects after a mean time of 425.0±180.7 min.

TABLE 8

| Subject No | Onset of release (min) | Site of onset | Completion of release (min) | Site of completion |
|---|---|---|---|---|
| 001 | 112.5 | S | 562.5 | TC |
| 002 | 82.5 | SI | 697.5 | DC |
| 003 | 67.5 | SI | 517.5 | AC |
| 004 | 82.5 | S | 367.5 | AC |
| 005 | 52.5 | SI | 652.5 | TC |
| 006 | 52.5 | S | 202.5 | TC |
| Mean | 75.0 | | 500.0 | |
| Median | 75.0 | | 540.0 | |
| Min | 52.5 | | 202.5 | |
| Max | 112.5 | | 697.5 | |
| St Dev | 22.7 | | 185.8 | |
| N | 6 | 3 S; 3 SI | 6 | 2 AC; 3 TC; 1 DC |

S—stomach; SI—small intestine; AC—ascending colon; TC—transverse colon; DC—descending colon The above table shows site and time of radiolabel release from the sustained release portion of the triphasic release tablet in healthy volunteers (n=6). The release are visualised for subject 4 in the second arm study in FIG. 7.

The utility of the present invention can be clearly seen from the finding of this study that onset of release times for both the sustained release layer and burst release core were highly reproducible, as evidenced by the small standard deviation times of 22.7 min and 13.4 min respectively.

FIG. 8 shows the mean erosion profile of the tablet in vitro and in vivo, demonstrating close IVIVC (in vitro and in vivo correlation). The Y axis provides percentage released radiolabeled therapeutic agent of the total in the tablet. Data established according to the methods of 2. above.

The invention claimed is:

1. A method of forming an erodible sustained release tablet comprising:
   a. mixing one or more therapeutic agents, one or more disintegrants and one or more molten waxes, whilst retaining the wax in molten form to form a mixture, and wherein the one or more waxes and the one or more disintegrants are mixed in a wax:disintegrant ratio of 7:1 to 1:1.13;
   b. solidifying and granulating the mixture; and
   c. forming the tablet by compression of the granules, and wherein the therapeutic agent has a constant rate of release.

2. The method of claim 1, wherein the compressed granules of step c. entirely form the sustained release tablet.

3. The method of claim 1, wherein the compressed granules of step c. form an erodible sustained release core of the tablet, and wherein the tablet further comprises one or more functionalised layer encapsulating the core.

4. The method of claim 3, wherein the one or more functionalised layers encapsulating the core are enteric coatings or immediate release coatings.

5. The method of claim 1, wherein the compressed granules of step c. form an erodible sustained release layer that encapsulates a core of a tablet.

6. The method of claim 1, wherein the wax is carnauba wax, paraffin wax, castor wax, beeswax, glycerol behenate, a glycowax or any combination thereof.

7. The method of claim 1, wherein the wax is present from about 20% to 80% by weight of the compressed granules of step c.

8. The method of claim 1, wherein the disintegrant is a low substituted hydroxypropyl cellulose.

9. The method of claim 1, wherein the disintegrant is LH-11, LH-21, LH-22, LH-32, NBD-021, NBD-020, LH-B1 or any combination thereof.

10. The method of claim 1, wherein the disintegrant is present from about 10-80% by weight of the compressed granules of step c.

11. The method of claim 1, wherein the mixing comprises mixing only a therapeutic agent, a disintegrant and a molten wax in step a.

12. A sustained release tablet comprising a wax, a disintegrant and a therapeutic agent,
   wherein the wax substantially coats particles or agglomerates of the therapeutic agent and of the disintegrant,
   wherein the wax and the disintegrant are present in a ratio of 7:1 to 1:1.13, and
   wherein the therapeutic agent has a constant rate of release.

13. The sustained release tablet of claim 12, wherein the wax, the disintegrant and the therapeutic agent form a core of the tablet, and the tablet further comprises one or more functionalised layer encapsulating the core.

14. The sustained release tablet of claim 13, wherein the one or more functionalised layers encapsulating the core are enteric coatings or immediate release coatings.

15. The sustained release tablet of claim 12, wherein the wax, the disintegrant and the therapeutic agent form a layer that encapsulates a core of the tablet.

16. The sustained release tablet of claim 12, wherein the wax is carnauba wax, paraffin wax, castor wax, beeswax, glycerol behenate, a glycowax or any combination thereof.

17. The sustained release tablet of claim 12, wherein the wax is present from about 20% to 80% by weight of a mixture comprising the wax, the disintegrant, and the therapeutic agent.

18. The sustained release tablet of claim 12, wherein the disintegrant is low substituted hydroxypropyl cellulose.

19. The sustained release tablet of claim 12, wherein the disintegrant is LH-11, LH-21, LH-22, LH-32, NBD-021, NBD-020, LH-B1, or any combination thereof.

20. The sustained release tablet of claim 12, wherein the disintegrant is present from about 10-80% by weight of a mixture comprising the wax, the disintegrant, and the therapeutic agent.

21. A sustained release tablet consisting of a wax, a disintegrant and a therapeutic agent,
   wherein the wax substantially coats particles of the therapeutic agent and of the disintegrant,
   wherein the wax and the disintegrant are present in a ratio of 7:1 to 1:1.13, and
   wherein the therapeutic agent has a constant rate of release.

* * * * *